(12) United States Patent
Undheim et al.

(10) Patent No.: US 8,304,531 B2
(45) Date of Patent: Nov. 6, 2012

(54) PROCESS FOR THE PREPARATION OF AN (RP)-8-SUBSTITUTED CAMPS

(75) Inventors: Kjell Undheim, Oslo (NO); Mioara Andrei, Oslo (NO)

(73) Assignee: Solvell AS, Oslo (NO)

( * ) Notice: Subject to any disclaimer, the term of this patent is extended or adjusted under 35 U.S.C. 154(b) by 678 days.

(21) Appl. No.: 12/441,317

(22) PCT Filed: Sep. 17, 2007

(86) PCT No.: PCT/GB2007/003522
§ 371 (c)(1),
(2), (4) Date: Aug. 5, 2009

(87) PCT Pub. No.: WO2008/032103
PCT Pub. Date: Mar. 20, 2008

(65) Prior Publication Data
US 2010/0137237 A1 Jun. 3, 2010

(30) Foreign Application Priority Data
Sep. 15, 2006 (GB) .................................. 0618235.6

(51) Int. Cl.
*C07H 21/00* (2006.01)

(52) U.S. Cl. ..................................... 536/25.31; 536/25.3
(58) Field of Classification Search .................... None
See application file for complete search history.

(56) References Cited

FOREIGN PATENT DOCUMENTS

| | | |
|---|---|---|
| JP | 2002-501499 A | 1/2002 |
| WO | 93/21929 A1 | 11/1993 |
| WO | 98/48809 A1 | 11/1998 |
| WO | 03/104250 A1 | 12/2003 |
| WO | 2005/123755 A2 | 12/2005 |

OTHER PUBLICATIONS

Baraniak et al. J. Chem. Soc. Perkin Trans. 1 (1987), pp. 1645-1656.*

* cited by examiner

Primary Examiner — Patrick Lewis
(74) Attorney, Agent, or Firm — Sughrue Mion, PLLC

(57) ABSTRACT

This invention relates to a process for the preparation of an (Rp)-8-substituted adenosine-3',5'-cyclic phosphorothioic acid, or a salt or ester thereof, which comprises P-amidating 8-bromoadenosine-3',5'-cyclic phosphoric acid, and reacting the P-amidate with a base and with carbon disulphide to yield (Rp)-8-bromoadenosine-3',5'-cyclic phosphorothioic acid or a salt or ester thereof.

8 Claims, No Drawings

PROCESS FOR THE PREPARATION OF AN (RP)-8-SUBSTITUTED CAMPS

This invention relates to a novel process for the preparation of an (Rp)-8-substituted adenosine-3',5'-cyclic phosphorothioic acid or a derivative thereof.

The naturally occurring purine cyclic monophosphates, cyclic adenosine monophosphate (cAMP) and cyclic guanosine monophosphate (cGMP), are messenger molecules important for mediating the effects on cell function of hormones.

It has been proposed that analogues of such cyclic nucleotides may be used in treating disease states associated with reduced or enhanced immune function. Thus one such analogue is adenosine cyclic monophosphorothioate (cAMPS), or more exactly adenosine 3',5'-cyclic monophosphorothioate, in which one of the oxygens pendant from the phosphorus atom is replaced by a sulphur. The phosphorus as a result is a chiral centre, and in the Rp configuration (at the phosphorus atom) cAMPS is a cAMP antagonist while in the Sp configuration (at the phosphorus atom) it is a cAMP agonist.

The use of (Rp)-cAMPS as a cAMP antagonist as part of an HIV treatment has been proposed for example in WO98/48809 and the use of cAMPS as an inhibitor of neoplastic growth has been proposed in U.S. Pat. No. 5,843,916.

Various 8-hetero-substituted (Rp)-cAMPS compounds are known in the art and include the bromo, chloro and iodo compounds. Also known are 8-substituted —OH derivatives, —SR derivatives wherein R is methyl, ethyl, isopropyl, phenyl or substituted phenyl, —NHR derivatives wherein R is hexane or cyclopropane, and 8-piperidino cAMPS.

Processes for the production of 8-substituted cAMPS are known from, inter alia, WO 2005/123755 which describes the introduction of an 8-carbyl substituent into the cAMPS by four methods: In the first, an 8-halogenated 3'5'-cyclic phosphoramidate is 8-carbylated whereafter the phosphorus-attached nitrogen is replaced by a sulphur in a reaction which retains the configuration of the chiral phosphorus; in the second and third an adenosine is 8-carbylated whereafter the cyclic phosphorus group is introduced; and in the fourth an 8-halo-cAMPS is 8-carbylated.

We have now surprisingly found that disadvantages associated with the methods known in the art for the preparation of 8-substituted (Rp)-cAMPS, in particular the partial 8-exchange of bromine with, for example, chlorine during certain reaction steps, may be significantly reduced or even prevented by the choice of specific reagents and reaction conditions. The method described hereinafter enables the conversion of a phosphoramidate intermediate into its phosphorothioate analogue without significant unwanted further substitution at the 8-position during the conversion, thereby producing a substantially pure product which may be further substituted in a controlled manner at the 8-position if desired.

Thus viewed from one aspect the invention provides a process for the preparation of an (Rp)-8-substituted adenosine-3',5'-cyclic phosphorothioic acid or a derivative thereof which comprises P-amidating 8-bromoadenosine-3',5'-cyclic phosphoric acid, and reacting the P-amidate with a base and with carbon disulphide to yield (Rp)-8-bromoadenosine-3',5'-cyclic phosphorothioic acid or a salt or ester thereof. The P-amidation is preferably achieved by reaction with an optionally substituted primary amine, e.g. an aryl-, alkyl- or aralkyl-amine, particularly preferably benzylamine.

The conversion of compounds produced by, or involved in, processes according to the invention between the acid form and ester or salt derivative forms would be readily appreciated by the skilled person to be possible at any stage of the process. As such, references to phosphoric or phosphorothioic acids are also intended to encompass the ester or salt derivatives thereof.

Examples of (Rp)-8-substituted-cAMPSs that may be generated by the process of the present invention include the compounds of Formula I:

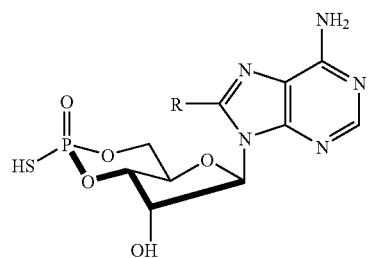

(wherein
R denotes F, Br, Cl or I or $R^1Z$ wherein $R^1$ denotes:
(1) a $C_{1-6}$-alkyl, which may be straight or branched, or $C_{3-7}$-cycloalkyl, $C_{2-6}$-alkylene or $C_{5-8}$-cycloalkylene, wherein any of the groups may have a heteroatom inserted, i.e. be part of an ether as an oxa derivative, a sulphide as a thia derivative which may be oxidised to a sulfoxide or sulfone or an amine as an aza derivative;
(2) a $C_{3-10}$-aryl or $C_{3-10}$-heteroaryl which may be reduced at one or more carbon atoms or heteroatoms, e.g. by hydrogen or deuterium, to yield a partially reduced aryl or heteroaryl group; or
(3) an $NHR^2$ group wherein $R^2$ is defined as $R^1$ under (1) and (2) above but also denotes $C_{1-4}$—CO, $C_{5-8}$-aryl-CO or $C_{5-8}$-heteroaryl-CO where aryl or heteroaryl are defined as above under (2))
and salts and esters thereof.

In Formula I above any heteroaryl system will comprise at least one heteroatom chosen independently from the group consisting of oxygen, sulphur and nitrogen.

The $R^1$-groups defined above may also be independently substituted by one or more halogens, hydroxy groups including alkylated, arylated, heteroarylated or acylated hydroxy derivatives and their sulphur analogues and/or amino groups themselves substituted as above or acylated in the form of an amide or urethane, carboxylic acids, or esters or amides thereof and/or by oxo groups in the ring or chains.

In one embodiment of the present invention the 2'-hydroxyl group of the (Rp)-8-substituted adenosine-3',5'-cyclic phosphoric acid is protected by a protecting group during some, or all of the process. Preferably the 2'-hydroxyl group of the (Rp)-8-substituted adenosine-3',5'-cyclic phosphoric acid is protected by a protecting group before the P-amidation and deprotected subsequent to the reaction with carbon disulphide. Preferably the protecting group is a silyl protecting group, particularly preferably a tert-Butyldimethylsilyl (TBDMS) protecting group.

The base used in the process of the invention is preferably a strong base, especially an N-metalated amine wherein the metal is lithium, magnesium, zinc, sodium, potassium or caesium.

Particularly preferred are lithium amides derived from secondary amines having a pKa value greater than 30, for example greater than 31, preferably greater than 32, more preferably greater than 33 or especially greater than 34, e.g. having a pKa value between 30 and 35, for example the lithium amides derived from $HNR^1R^2$ wherein $R^1$ and $R^2$ may be the same or different and are selected from the group consisting of optionally substituted $C_{1-6}$-alkyl, $C_{3-6}$-cycloalkyl, phenyl and tri($C_{1-3}$-alkyl)silyl, or wherein N, together with $R^1$ and $R^2$, forms an optionally substituted 5- or 6-membered heteroaromatic monocyclic group. Especially preferred as strong bases are metal hydrides (e.g. lithium, sodium or potassium hydrides, especially sodium hydride), dimethylamine, diethylamine, pyrrole, diphenylamine, di-sec-butylamine, diisopropylamine, dicyclohexylamine, N-isopropyl-N-cyclohexylamine, bis-trimethylsilylamine, 2,2,6,6-tetramethylpiperidine, N-isopropyl-N-trimethylsilylamine, N-neopentyl-N-trimethylsilylamine and N-tert-butyl-N-trimethylsilylamine.

Other N-metalated amines derived from amines having similar pKa values may also be used. Thus, also particularly preferred are magnesium amide bases derived from the above-mentioned secondary amines. These may be used either as their monoamine salts (for example bromo(diisopropylamino)magnesium) or as diamines (for example magnesium bis(diisopropylamine)) or preferably as $C_{1-6}$-alkylmagnesium amides (for example butyl-magnesium diisopropylamine).

Also particularly preferred are mixed lithium/magnesium amides of the type $R^1R^2NMgCl.LiCl$ wherein $R^1$ and $R^2$ are as hereinbefore defined. Especially preferred examples are mixed amides of the above formula wherein $R^1$ and $R^2$ are i-propyl or wherein N, $R^1$ and $R^2$ together form a 2,2,6,6-tetramethylpiperidino salt.

Also particularly preferred are zinc amide bases derived from the above-mentioned secondary amines. Lithium (di-tert-butyl-2,2,6,6-tetramethylpiperidino)zincate is an especially preferred example.

Also particularly preferred are the so-called "superbases", composite bases of organolithium derivatives and heavier alkali metal alkoxides, e.g. n-butyllithium-potassium-tert-butoxide.

Other examples of strong bases that may be used according to the invention include potassium or sodium tert-butoxide and sterically hindered $C_{1-6}$-alkyllithium derivatives such as tert- or sec-butyllithium, in some cases n-butyllithium may be used. Also preferred as the metal is magnesium e.g. in the form of alkylmagnesium halides, preferably iso-propyl magnesium chloride.

The deprotonation of the phosphoramidate intermediate using a strong, non-nucleophilic base as hereinbefore defined is preferably carried out in a convenient solvent compatible with the base chosen, such as dimethylformamide, dichloromethane or an ether type solvent such as tetrahydrofuran, at a temperature of between $-100°$ C. and $100°$ C., for example between $-80°$ C. and ambient temperature, preferably between $-78°$ C. and $0°$ C., more especially between $-50°$ C. and $-10°$ C. and for a length of time between 1 minute and 3 hours, preferably between 10 minutes and 2 hours, especially between 30 and 90 minutes.

The (Rp)-8-bromoadenosine-3',5'-cyclic phosphorothioic acid or the salt or ester thereof produced by the above process may then be substituted at the 8-position. In a preferred embodiment, the process of the present invention therefore further comprises the step of replacing the bromine at the 8-position with an alternative substituent group. This alternative substituent group may for example be a thiol, an alcohol or phenol or a primary or secondary amine. The alternative substituent group may be introduced using methods known in the art, e.g. nucleophilic substitutions.

This heteronucleophilic substitution of bromine may conveniently be carried out following the masking of the phosphorothioic acid functionality by, for example, protecting the sulphur atom by attachment of a protecting group. This S-protecting group is preferably an alkyl group, particularly preferably a p-nitrobenzyl group which may be introduced by e.g. alkylation with benzyl bromide. The S-protecting group is preferably removed after the substitution has taken place. In the case where the protecting group is a p-nitrobenzyl group, the deprotection may be effected under mild conditions using dilute sodium hydroxide or more preferably 1,8-diazabicyclo[5.4.0]undec-7-ene (DBU) or congeners thereof in the presence of a thiol such as p-thiocresol.

The 8-substituted (Rp)-cAMPS produced by the above method may be formulated into a pharmaceutical composition. Another embodiment of the present invention therefore contemplates a process for the preparation of an (Rp)-8-substituted adenosine-3',5'-cyclic phosphorothioic acid, or a salt or ester thereof, further comprising the step of formulating the (Rp)-8-substituted adenosine-3',5'-cyclic phosphorothioic acid or salt or ester thereof into a pharmaceutical composition by admixing with one or more pharmaceutically acceptable carriers or excipients. Preferably the salt or ester of the (Rp)-8-substituted adenosine-3',5'-cyclic phosphorothioic acid is a physiologically tolerable salt or ester thereof.

Viewed from a further aspect, therefore, the invention provides a pharmaceutical composition comprising a physiologically tolerable 8-substituted (Rp)-cAMPS or a derivative thereof produced by the process of the invention together with a pharmaceutically acceptable carrier or excipient.

The composition of the invention may take any convenient administration form, e.g. tablet, capsule, powder, syrup, spray, solution, dispersion, suppository, etc. The active agent will be admixed with one or more pharmaceutically acceptable carriers or excipients, e.g. a solvent (such as water for injections), diluent, stabilizer, viscosity modifier, pH modifier, aroma, flavour, antioxidant, etc. and the composition may be prepared in conventional fashion.

By the term "salts" of compounds produced according to the present invention or used in the process of the present invention is meant internal salts, if the compound has a suitable basic group such as e.g. an amino function, or salts with inorganic or organic acids or bases. Preferred are the salts with physiologically tolerable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid and citric acid. Also preferred are the salts with physiologically tolerable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine and dicyclohexylamine, inter alia.

The invention will now be further illustrated by the following non-limiting examples:

EXAMPLE 1

Preparation of the Starting Material (Scheme A)

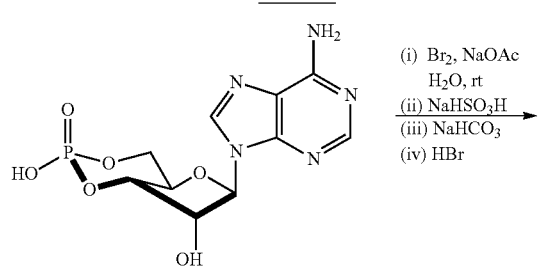

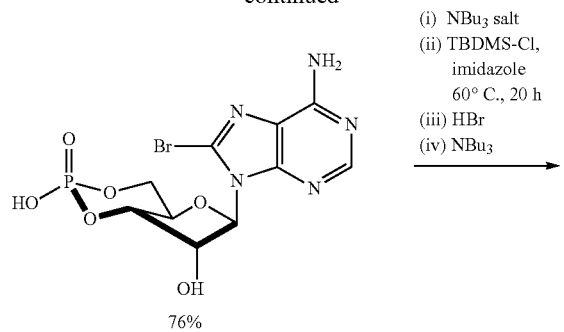

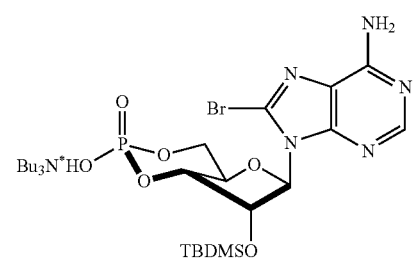

The starting material was commercially available cAMP. Bromination on a large scale, as previously described in WO 2005/123755, furnished the 8-bromo derivative. The 2'-OH group of the ribose was subsequently protected by a bulky silyl group to furnish the intermediate silyloxy derivative. Among other things, the silyl group affects relative solubilities. The respective silyl chloride was employed for the silylation which is best carried out at low temperature to avoid a halogen exchange where the chloride ion would displace the bromide substituent (the chloride ion originates from the silyl chloride reagent). Low temperature during the reaction and neutralization of the reaction medium before the reaction is worked up avoids halogen exchange. As an alternative the respective silyl triflates could be used to exclude halogen interchange.

EXAMPLE 2

Preparation of (Rp)-8-bromoadenosine-3',5'-cyclic phosphorothioic acid (Scheme B)

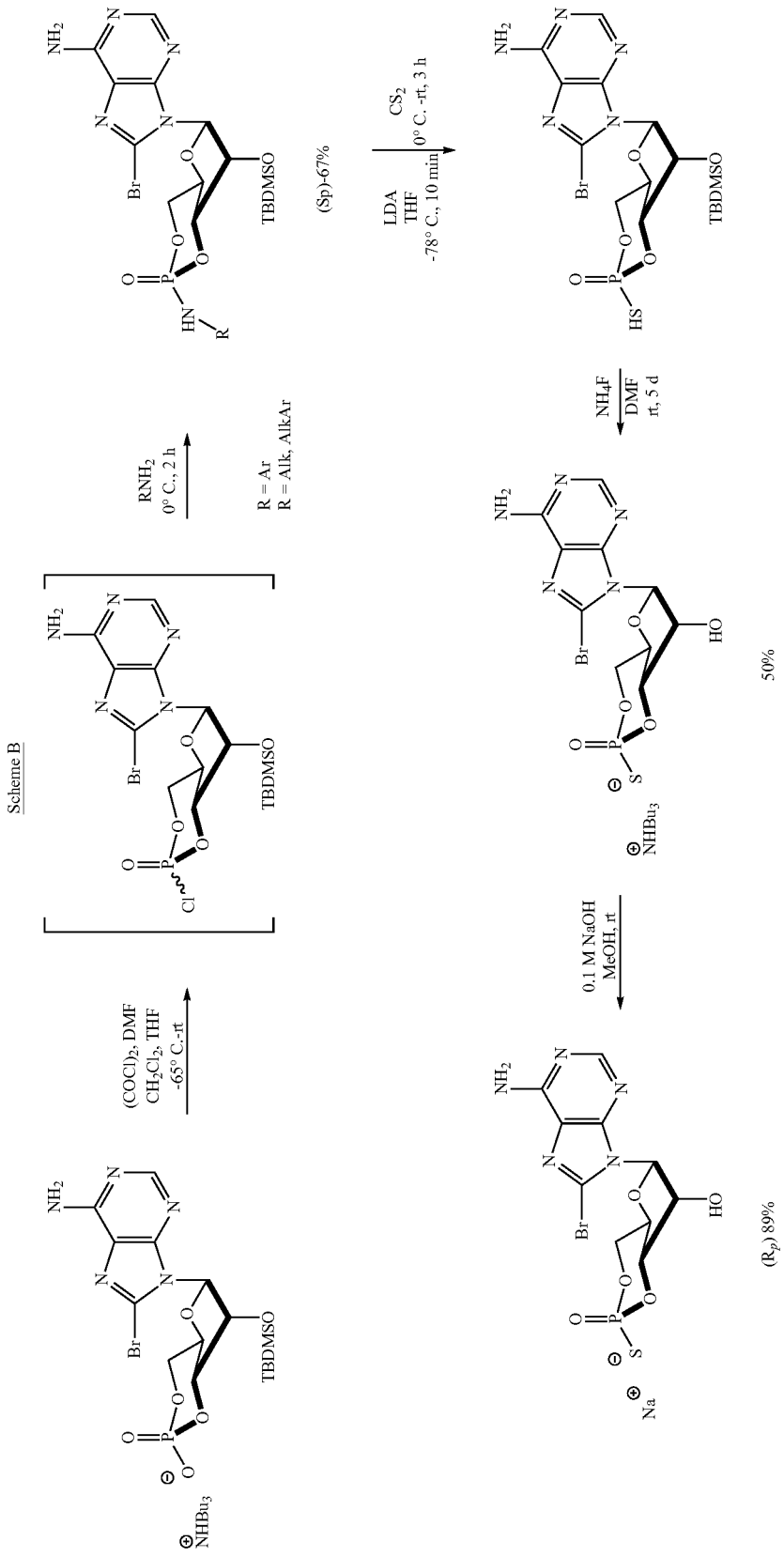

The substrate is the silyl-protected bromide from Scheme A (Example 1). Amidation is effected via an initial activation of the phosphoric acid using oxalyl chloride and DMF in dichloromethane and THF at low temperature. Subsequent treatment with an amine provides the amidate. Only the (Sp)-isomer was isolated. Either an arylamine such as aniline, or an alkylamine, such as benzylamine was used for the amination. The choice of amine may depend on the reactivity of the 8-substituent. A strong base is used to abstract an amido hydrogen in the amidate. The metal amidate is subsequently treated with carbon disulfide to form an adduct. A subsequent rearrangement leads to generation of the phosphorothioate.

The silyl protection can be cleaved by fluoride ions, e.g. using ammonium fluoride in DMF (between 3 and 5 days at room temperature) or using caesium fluoride (a few hours at room temperature).

The phosphorothioic acid can be purified as an ammonium salt, preferably as the tributylammonium salt which may be converted, if desired, into an alkalimetal salt simply by the addition of a metal hydroxide, e.g. sodium hydroxide.

When aniline was used for amidation, the yield was in the range 40-60%; with benzylamine the yield was in the range 60-80%. Potassium tert-butoxide was the base used for the thiylation of an anilidate, for benzylamidate a lithium amide base, commonly LDA, was used.

EXAMPLE 3

8-substitution of (Rp)-8-bromoadenosine-3',5'-cyclic phosphorothioic acid (Scheme C)

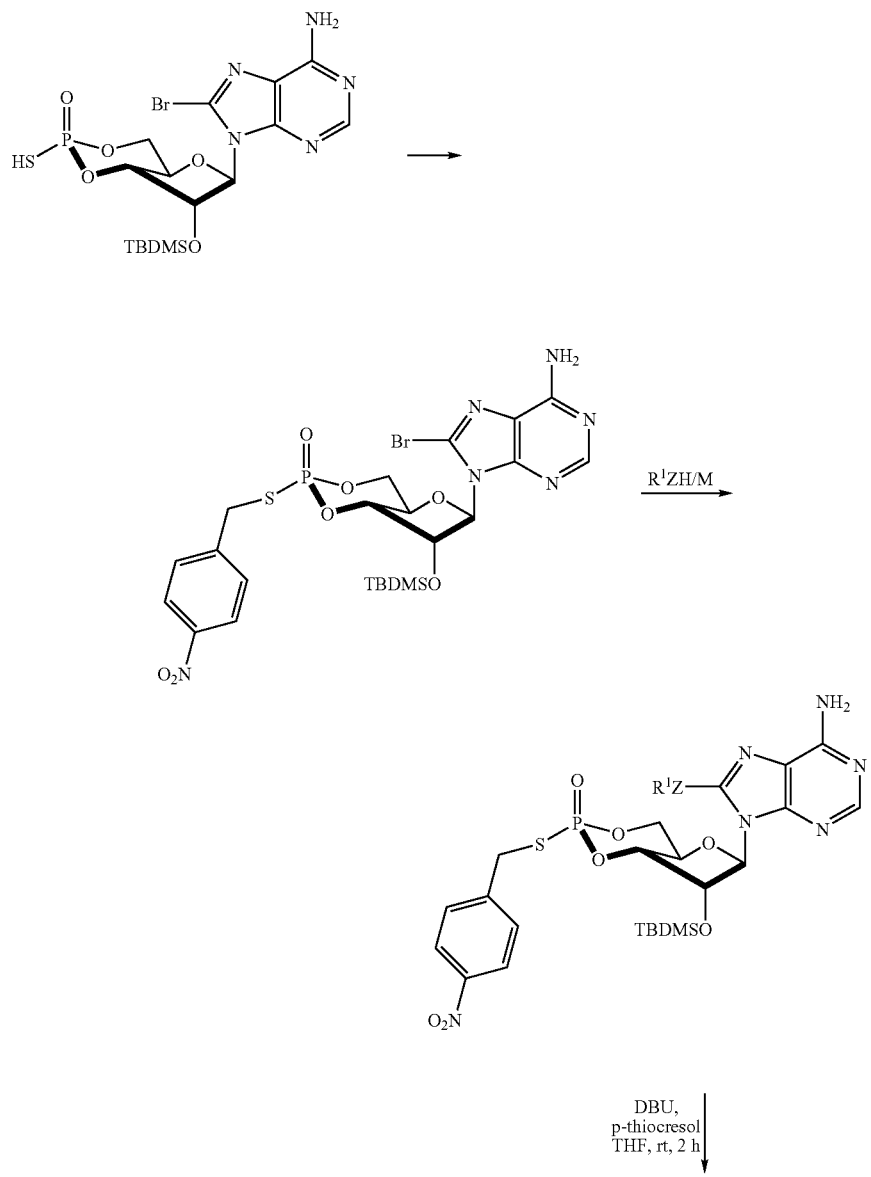

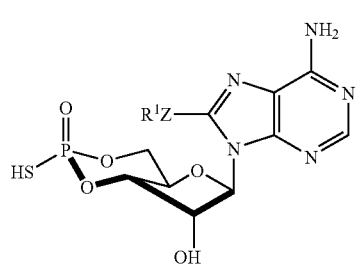 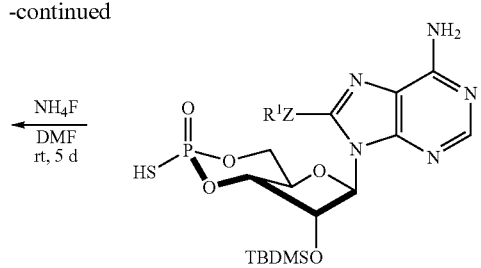

A stereochemically pure 8-bromo- or 8-chloro-cAMPS is used as a substrate for introduction of the heterosubstituent into the 8-position in the phosphorothioate derivative. In principle, several families of derivatives become available from the one halogeno substrate which was stereoselectively produced via the corresponding amidate. Heteronucleophilic and regioselective substitution of the bromine in the 8-position in the purine ring at the phosphorothioic acid stage may be a challenge because of the reactivity of the sulphur in the phosphorothioic acid moiety. In most cases, prior S-protection will be advantageous or necessary as illustrated in scheme C. In this case the silyl protecting group is retained until the final step. The overall stability may be improved if the silyl group is removed at an earlier step so that it is the free hydroxyl compound which is taken to the final stage according to Scheme D:

Scheme D

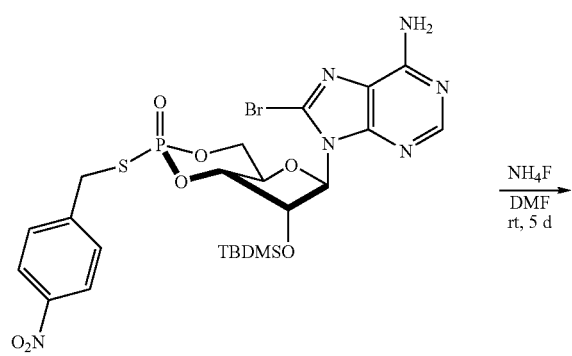

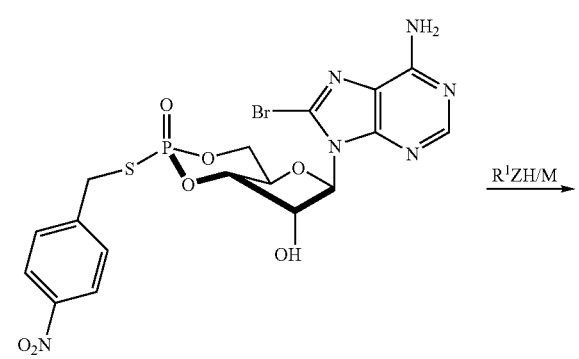

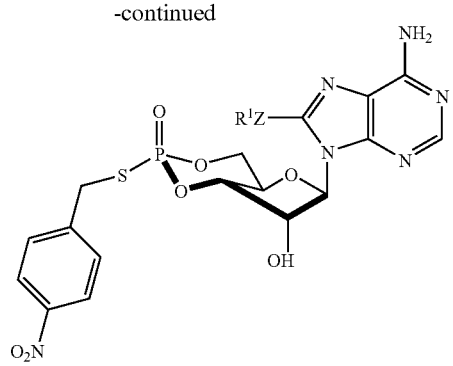

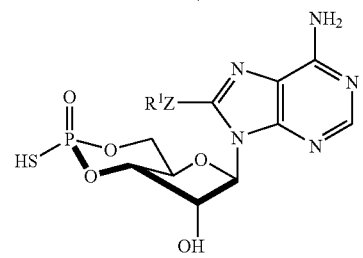

EXAMPLE 4

8-Bromoadenosine-3',5'-cyclic phosphoric acid

Bromine (15.4 ml, 0.30 mol) was added with stirring to a solution of cAMP (98.8 g, 0.30 mol) and sodium acetate trihydrate (81.6 g, 0.60 mol) in water (1.5 l) over 1 h at room temperature. After 24 h, sodium sulphite was added slowly until disappearance of the dark red colour. The precipitate was collected by filtration, the solid washed with water, 2-propanol and diethyl ether before being dried at reduced pressure. The product was dispersed in water (500 ml) and dissolved by slow addition of sodium bicarbonate (1 equiv.). When all the material had dissolved, small portions of sodium sulphite were added to remove the dark red colour of the solution. Precipitation of the product was effected by dropwise addition of 1.0 M hydrobromic acid under vigorous stirring. The precipitate was collected, washed with water, 2-propanol, diethyl ether and the bright yellow powder dried under high vacuum.

Yield 92.0 g (76%).

$^1$H NMR was in accordance with the literature.

EXAMPLE 5

2'-O-(tert-Butyldimethylsilyl)-8-bromadenosine-3',5'-cyclic phosphoric acid tributylammonium salt (a) Using TBDMS-Cl TBDMS-Cl (2.72 g, 18 mmol) was added to a solution of 8-Br-cAMP tributylammonium salt (Example 4) (7.0 g, 11.8 mmol) and imidazole (2.45 g, 36 mmol) in DMF (30 ml) at room temperature. The mixture was stirred at 60° C. for 20 h under argon. The solvent was removed at reduced pressure, the residual material suspended in water (150 ml), stirred for 30 min to hydrolyse any silylated phosphoric acid and 1 M HBr (ca 12 ml, till pH 2-3) was added to the filtrate. The precipitate was filtered off, washed with water and dried under vacuum. The acid was suspended in MeOH (80 ml) and $Bu_3N$ (5 ml) was added. The mixture was stirred at room temperature until a clear solution was obtained (30 min), the solvent distilled off and the residual product dried under vacuum over $P_2O_5$ before being used as such in the subsequent reaction.

Yield 6.60 g (78%) of a white solid.

HRMS (Electrospray): Found negative ions: M 520.0427. Calc. 520.0422.

$^1$H NMR (DMSO-$d_6$, 300 MHz): δ 0.01 (3H, s, Si—$CH_3$), 0.03 (3H, s, Si—$CH_3$), 0.83 (9H, s, Si-t-Bu), 0.87 (9H, t), 1.28 (6H, m,), 1.53 (6H, m,), 2.79 (6H, m,), 3.90 (2H, m,), 4.11 (1H, m,), 5.02 (2H, m,), 7.53 (2H, s, $NH_2$), 8.15 (1H, s, H-2).

$^{13}$C NMR (DMSO-$d_6$, 75 MHz): δ −5.3, −4.7, 13.6, 18.0, 19.6, 25.6, 25.7, 51.9, 65.4, 72.3, 72.4, 76.2, 94.3, 119.2, 126.5, 150.0, 153.2, 155.0.

$^{31}$P-NMR (CDCl$_3$, 81 MHz): δ −1.36.

(b) Using TBDMS-Triflate

TBDMS-Triflate (4.75 g, 4.13 ml, 18 mmol) was added to a suspension of 8-Br-cAMP tributylammonium salt (Example 4) (5.3 g, 8.9 mmol) and imidazole (1.72 g, 27 mmol) in $CH_2Cl_2$ (40 ml) at room temperature. The mixture was stirred for 20 h under argon. The solvent was removed, the residual material suspended in water (120 ml), stirred for 30 min to hydrolyse any silylated phosphoric acid and 1 M HBr (ca 10 ml, till pH 2-3) was added to the filtrate. The precipitate was filtered off, washed with water and dried under vacuum. The acid was suspended in MeOH (60 ml) and $Bu_3N$ (4 ml) was added. The mixture was stirred at room temperature until a clear solution was obtained (30 min), the solvent distilled off and the residual product dried under vacuum over $P_2O_5$ before being used as such in the subsequent reaction.

Yield 4.93 g (78%) of a white solid with physical data as above.

EXAMPLE 6

(Sp)-8-Bromoadenosine-2'-O-(tert-butyldimethylsilyl)-3',5'-cyclic N-benzylphosphoramidate Dry DMF (0.385 ml, 5.00 mmol) in dry $CH_2Cl_2$ (40 ml) was placed under an atmosphere of argon gas and cooled to 0° C. before oxalyl chloride (3 ml, 2 M in $CH_2Cl_2$, 6.0 mmol) was added slowly. The cooling bath was removed and the suspension stirred at room temperature for 30 min, the reaction mixture cooled to −65° C. and a solution of tributylammonium 8-bromoadenosine-2'-O-TBDMS-3',5'-cyclic monophosphate (Example 5) (4.750 g, 6.7 mmol) in dry $CH_2Cl_2$ (3 ml) was added through a teflon tube. The mixture was stirred at this temperature for 1 h before dry ($CaH_2$) benzylamine (2.84 ml, 26.8 mmol) was added slowly. The cooling bath was removed after 1 h and the reaction mixture stirred at room temperature for 2 h, the turbid reaction mixture diluted to 120 ml with $CH_2Cl_2$ and shaken with cold, saturated sodium hydrogen carbonate (2×50 ml). The organic phase was dried over $MgSO_4$, the solvent removed at reduced pressure and the residual material was subjected to flash chromatography on silica gel using 4% methanol in $CH_2Cl_2$.

Yield 2.0 g (49%) of a white solid.

TOF MS ES$^+$: 611.1/613.1.

$^{31}$P (CDCl$_3$, 121 MHz): δ 8.29; $^1$H NMR (CDCl$_3$, 200 MHz): δ 0.03 and 0.04 (6H, 2 s, 2×Si-Me), 0.84 (9H, s, Si-tBu), 3.61-3.68 (1H, m), 4.13-4.21 (3H, m,), 4.35-4.56 (2H, m), 5.0 (1H, d, J 5.1 Hz,), 5.62-5.70 (1H, m,), 5.85 (2H, bs, $NH_2$), 5.91 (1H, s,), 7.25-7.33 (5H, m,), 8.21 (1H, s, H-2).

EXAMPLE 7

(Rp)-8-Bromoadenosine-2'O-(tert-butyldimethylsilyl)-3',5'-cyclic phosphorothioic acid A 1.8 M solution of LDA in THF/heptane/diethyl ether (2 ml, 3.6 mmol) was added to a solution of (Sp)-8-bromoadenosine-2'-O-(tert-butyldimethylsilyl)-3',5'-cyclic N-benzylphosphoramidate (Example 6) (2.0 g, 3.27 mmol) in dry THF (30 ml) at −78° C. The mixture was stirred at this temperature for 20 min before $CS_2$ (0.6 ml, 9.81 mmol) was added. The cooling bath was removed after 10 min. The reaction mixture was stirred at room temperature for 3 h before the solvent was partially removed on a rotary evaporator. Hexane was subsequently added until the precipitation was complete. The precipitate was dissolved in water (50 ml) and 1 M HBr (3.3 ml) was added at 0° C. The (Rp)-8-bromoadenosine-3',5'-cyclic phosphorothioic acid was collected by filtration and dried overnight at high vacuum.

EXAMPLE 8

(Rp)-8-Bromoadenosine-3',5'-cyclic phosphorothioic acid tributylammonium salt

A solution of the dried thioic acid product (Example 7) (1.70 g, 3.16 mmol) in DMF (15 ml) was stirred together with $NH_4F$ (0.750 g) at room temperature for 5 days. The reaction mixture was filtered, $NBu_3$ (1.11 g, 6 mmol) was added to the clear solution and the solvent was removed at reduced pressure. The residue was washed with hexane to remove excess of $NBu_3$ and the residual material subjected to flash chromatography on silica gel using $CH_2Cl_2$:$CH_3OH$:$NBu_3$ 100:10:1.

The ammonium salt, which contains some NBu₃, was further purified by dissolution in CH₂Cl₂ and precipitation by hexane and isolated by filtration.

Yield 1.105 g (50% from substrate of Example 5) of a white solid.

TOF MS ES⁻: 421.9/423.9;

$^{31}$P (CDCl₃, 121 MHz): δ 57.28;

$^{1}$H NMR (CDCl₃, 200 MHz): δ 0.85-0.97 (9H, m,), 1.23-1.44 (6H, m,), 1.67-1.76 (6H, m,), 2.97-3.05 (6H, m,), 4.30-4.42 (3H, m,), 5.05 (3H, d, J 5 Hz, 1H), 5.27 5.45 (1H, m), 5.91 (1H, bs, NH₂), 5.98 (1H, s,), 8.18 (1H, s, H-2).

EXAMPLE 9

(R$_P$)-8-bromoadenosine-3',5'-cyclophosphorothioic acid sodium salt (R$_P$)-8-Bromoadenosine-3',5'-cyclic phosphorothioate tributylammonium salt (Example 8) (1.0 g, 1.64 mmol) was dissolved in 0.1 M NaOH in MeOH (17 ml). The sodium salt was precipitated by addition of diethyl ether and collected by filtration.

Yield 0.650 g (89%) of a white, solid material.

MS ES⁻: 421.9/423.9;

$^{31}$P (MeOD, 121 MHz): δ 57.96;

$^{1}$H NMR (MeOD, 200 MHz): δ 4.19-4.35 (3H, m,), 5.02 (1H, d, J 5.4 Hz), 5.38-5.46 (1H, m), 5.94 (1H, s), 8.18 (1H, s, H-2).

EXAMPLE 10

(Sp)-8-Chloroadenosine-2'O-(tert-butyldimethylsilyl)-3',5'-cyclic N-benzylphosphoramidate Dry DMF (0.32 ml, 4.24 mmol) in dry CH₂Cl₂ (50 ml) was placed under an atmosphere of argon gas and cooled to 0° C. before oxalyl chloride (14.2 ml, 2 M in CH₂Cl₂, 28.25 mmol) was added slowly. The cooling bath was removed and the suspension left stirring at room temperature for 30 min, the reaction mixture cooled to 0° C. and a solution of tributylammonium 8-bromoadenosine-2'-O-TBDMS-3',5'-cyclic monophosphate (4.0 g, 5.65 mmol) in dry CH₂Cl₂ (10 ml) was added through a teflon tube. The mixture was stirred at this temperature for 1 h, allowed to reach room temperature and the solvent removed at room temperature. The solid material was dissolved in CH₂Cl₂ (30 ml) and dry (CaH₂) benzylamine (3.7 ml, 33.9 mmol) added at 0° C. under argon. The cooling bath was removed after 10 min and the reaction mixture stirred at room temperature for 2 h. The turbid reaction mixture was filtered, the filtrate diluted to 80 ml with CH₂Cl₂ and washed with cold, saturated sodium hydrogen carbonate (2×25 ml). The organic phase was dried over MgSO₄, the solvent removed at reduced pressure and the residual material was subjected to flash chromatography on silica gel using 4% methanol in CH₂Cl₂.

Yield 2.2 g (68%) of a white solid.

TOF MS ES⁺: 567.1/669.1;

$^{31}$P (CDCl₃, 121 MHz): δ 8.29;

$^{1}$H NMR (CDCl₃, 200 MHz): δ 0.03 and 0.04 (2s, 6H 2×Si-Me), 0.84 (s, 9H, Si-tBu), 3.61-3.68 (m, 1H), 4.13-4.21 (m, 3H), 4.35-4.56 (m, 2H), 5.0 (d, J 5.1 Hz, 1H), 5.62-5.70 (m, 1H), 5.85 (bs, 2H, NH₂), 5.91 (s, 1H), 7.25-7.33 (m, 5H), 8.23 (s, 1H, H-2);

$^{13}$C NMR (CDCl₃, 75 MHz): −5.1, −4.7, 18.1, 25.5, 45.3, 68.2, 71.3, 73.0, 76.3, 93.5, 118.3, 127.1, 127.5, 128.5, 137.4, 138.7, 150.0, 153.5, 154.6.

EXAMPLE 11

(Rp)-8-Chloroadenosine-3',5'-cyclic phosphorothioic acid tributylammonium salt

A 1.8 M solution of LDA in THF/heptane/ethylbenzene (0.17 ml, 0.30 mmol) was added to a solution of (Sp)-8-chloroadenosine-2'-O-(tert-butyldimethylsilyl)-3',5'-cyclic-N-benzylphosphoramidate (Example 10) (0.160 g, 0.28 mmol) in dry THF (5 ml) at −78° C. The mixture was stirred for 20 min at this temperature before CS₂ (0.05 ml, 0.85 mmol) was added and the cooling bath removed after 10 min. The reaction mixture was stirred for 3 h at room temperature before the solvent was partially removed at the rotary evaporator. Hexane was added until total precipitation. The precipitate was dissolved in water (10 ml) and 1 M HBr (0.35 ml, pH 2-3) was added at 0° C. The resulting (Rp)-8-chloroadenosine-3',5'-cyclic phosphorothioic acid was collected by filtration and dried overnight.

A solution of the dried thioic acid (0.10 g, 0.2 mmol) in DMF (3 ml) was stirred together with NH₄F (0.050 g), at room temperature for 5 d. The reaction mixture was filtered, NBu₃ (0.090 g, 0.5 mmol) was added to the clear solution and the solvent was removed at reduced pressure. The residue was washed with hexane to remove the excess of NBu₃ and subjected to flash chromatography on silica gel using CH₂Cl₂: CH₃OH:NBu₃ 100:10:1. The ammonium salt, which contains NBu₃, was further purified by dissolution in CH₂Cl₂ and reprecipitation by addition of hexane.

Yield 0.070 g (ca 50% from the thioic acid) of a white solid.

TOF MS ES⁻: 378.1/380.1;

$^{1}$H NMR (CDCl₃, 200 MHz): δ 0.90-0.98 (m, 9H), 1.28-1.44 (m, 6H), 1.68-1.76 (m, 6H), 2.97-3.07 (m, 6H), 4.25-4.42 (m, 3H), 5.03 (d, J 5.2 Hz, 1H), 5.28-5.48 (m, 1H), 5.81 (bs, 2H, NH₂), 5.99 (s, 1H), 8.19 (s, 1H, H-2).

$^{13}$C NMR (CDCl₃, 75 MHz): 13.6, 20.1, 25.2, 51.9, 67.1, 71.7, 71.8, 76.2, 91.6, 118.5, 138.5, 150.3, 152.9, 154.1.

EXAMPLE 12

(R$_P$)-8-Chloroadenosine-3',5'-cyclic phosphorothioic acid sodium salt (Rp)-8-Chloroadenosine-3',5'-cyclic phosphorothioic acid tributylammonium salt (Example 11) (0.050 g, 0.073 mmol) was dissolved in 0.1 M NaOH (0.8 ml) in MeOH. The sodium salt was precipitated by addition of diethyl ether.

Yield 0.030 g (85%) of a white, solid material.

TOF MS ES⁻: 378.1/380.1;

$^1$H NMR (MeOH-d$_4$, 200 MHz): δ 4.25-4.45 (m, 3H), 5.02 (d, J 5.2 Hz, 1H), 5.28-5.45 (m, 1H), 6.02 (s, 1H), 8.2 (s, 1H, H-2).

$^{13}$C NMR (MeOH-d$_4$, 75 MHz): 59.1, 63.6, 64.25, 68.3, 84.5, 110.2, 129.8, 142.4, 145.3, 147.3.

The invention claimed is:

1. A process for the preparation of an (Rp)-8-substituted adenosine-3',5'-cyclic phosphorothioic acid, or a salt or ester thereof, which comprises P-amidating 8-bromoadenosine-3',5'-cyclic phosphoric acid, and reacting the P-amidate with a base and with carbon disulphide to yield (Rp)-8-bromoadenosine-3',5'-cyclic phosphorothioic acid or a salt or ester thereof, and wherein the base is a metal amide.

2. A process as claimed in claim 1 wherein the P-amidation is effected by reaction with benzylamine.

3. A process as claimed in claim 1 or 2 wherein the 2'-hydroxyl group of the (Rp)-8-substituted adenosine-3',5'-cyclic phosphoric acid is protected by a protecting group before the P-amidation and deprotected subsequent to the reaction with carbon disulphide.

4. A process as claimed in claim 3 wherein the protecting group is a silyl protecting group.

5. A process as claimed in claim 1 wherein the base is derived from a secondary amine having a pKa value of greater than 30.

6. A process as claimed in claim 5 wherein the base is lithium diisopropylamide.

7. A process as claimed in claim 1 or 2 further comprising the step of replacing the bromine at the 8-position with an alternative substituent group.

8. A process as claimed in claim 1 or 2 further comprising the step of formulating the (Rp)-8-substituted adenosine-3',5'-cyclic phosphorothioic acid or salt or ester thereof into a pharmaceutical composition by admixing with one or more pharmaceutically acceptable carriers or excipients.

* * * * *